United States Patent [19]

Flynn

[11] Patent Number: 4,581,390

[45] Date of Patent: * Apr. 8, 1986

[54] CATHETERS COMPRISING RADIOPAQUE POLYURETHANE-SILICONE NETWORK RESIN COMPOSITIONS

[76] Inventor: Vincent J. Flynn, 130 New Rd., Apt. D-10, Parsippany, N.J. 07054

[*] Notice: The portion of the term of this patent subsequent to Apr. 1, 2003 has been disclaimed.

[21] Appl. No.: 626,208

[22] Filed: Jun. 29, 1984

[51] Int. Cl.$^4$ .......................... A01N 1/00; A61F 2/00
[52] U.S. Cl. .................................... 523/112; 523/113; 523/121; 524/288; 524/506; 524/567; 428/36; 604/280
[58] Field of Search ...................... 524/506, 288, 567; 523/112, 113, 121; 604/280; 428/36

[56] References Cited

U.S. PATENT DOCUMENTS

| | | | |
|---|---|---|---|
| 2,823,218 | 2/1958 | Speier | 260/448.2 |
| 2,970,150 | 1/1961 | Bailey | 260/348 |
| 3,159,601 | 12/1964 | Ashby | 260/46.5 |
| 3,159,622 | 12/1964 | Ashby | 260/448.2 |
| 3,361,700 | 1/1968 | Archer | 260/31.4 |
| 3,645,955 | 2/1972 | Flynn | 260/31.4 |
| 3,752,617 | 8/1973 | Burlis | 425/131 |
| 4,242,287 | 12/1980 | Allen | 525/105 |
| 4,250,072 | 2/1981 | Flynn | 524/288 |
| 4,283,447 | 8/1981 | Flynn | 428/36 |

FOREIGN PATENT DOCUMENTS

961902  6/1964  United Kingdom .

OTHER PUBLICATIONS

Arkles & Carreno, "Silicone IPN Modified Thermoplastics", ANTEC '84, pp. 486–487.
Arkles, High Performance and Thermoplastic Silicones for Biomedical Applications, ANTEC '84, pp. 1080–1082.

*Primary Examiner*—Joseph L. Schofer
*Assistant Examiner*—N. Sarofim
*Attorney, Agent, or Firm*—Hedman, Gibson, Costigan & Hoare

[57] ABSTRACT

This invention relates to catheters prepared from novel radiopaque resin compositions and medical-surgical tubings. More particularly, the invention pertains to compositions of polyiodobenzoic acid ester-containing polyurethane resins, alone, or in combination with vinyl resins, and a platinum-cured silicone network polymer dispersed therein and their use in medical-surgical devices, especially tubing and catheters.

34 Claims, 6 Drawing Figures

CATHETERS COMPRISING RADIOPAQUE POLYURETHANE-SILICONE NETWORK RESIN COMPOSITIONS

This invention relates to catheters prepared from novel radiopaque resin compositions, and medical-surgical tubings containing such compositions. More particularly, the invention pertains to compositions of polyiodobenzoic acid ester-containing polyurethane resins, alone, or in combination with vinyl resins, and a platinum-cured silicone network polymer dispersed therein and their use in medical-surgical devices, especially tubing and catheters.

CROSS-REFERENCE TO RELATED APPLICATIONS

The present application is related to the following, concurrently-filed U.S. patent applications:

| Applicant | Serial No. | Subject Matter |
| --- | --- | --- |
| Vincent J. Flynn | 626,209 | Radiopaque Polyurethane-Silicone Network Resin Compositions and Medical-Surgical Tubings Prepared Therefrom |
| Vincent J. Flynn | 626,149 | Radiopaque Vinyl-Silicone Network Resin Compositions and Medical-Surgical Tubings Prepared Therefrom |

BACKGROUND OF THE INVENTION

Archer and Flynn, U.S. Pat. No. 3,361,700, disclose that a family of alkoxyalkyl esters of diiodobenzoic acid are radiopaque and suitable to plasticize vinyl resins into a form useful to manufacture tubings for catheters and similar products. Flynn, U.S. Pat. No. 3,645,955 discloses that di- and tetraiodoesters used alone or in combination with the alkoxyalkyl diiodoesters are superior for this purpose because they show less tendency to exude and lower concentrations provide a better balance between flexibility and stiffness. Burlis et al., U.S. Pat. No. 3,752,617 disclose methods for making multiwall tubing, co-tapered along its length, but use plastics other than polyurethane, and make no mention of any additives, specifically by name, to produce different X-ray sensitive characteristics. Copending U.S. application Ser. No. 514,168, of Vincent J. Flynn discloses thermoplastic, e.g., polyurethane, tubing rendered nonthrombogenic with a coating layer of silicone polymer.

While the iodoester opacified vinyl resin compositions of U.S. Pat. No. 3,361,700 are quite suitable for the production of tubing of simple types useful for intubation sets and catheter needles, they are not completely satisfactory for production of shaped devices. For example, if flared, or if formed into curved tips, the shapes tend to revert to straight tubing—a so-called loss of plastic memory effect. In applicant's U.S. Pat. Nos. 4,250,072 and 4,283,447, it is disclosed that if the vinyl resin is replaced partially or completely by thermoplastic polyurethane, the iodoester radiopacified compositions are amenable to the induction of complex shapes—and they'll stay that way. Such tubings provide catheters eminently suitable for selective renal arteriography and for celial arteriography, and also for the manufacture of pig-tail catheters. Surprisingly, the iodoesters do not show the same tendency to overplasticize the urethane esters as they do the vinyl esters, and, moreover, there is lesser need to use a radioparent plasticizer with urethanes and, in fact, it is preferred to omit a radioparent plasticizer completely. As is shown therein, the compositions lend themselves well to the formation of highly advantageous multi-wall tubing constructions. In one feature of the said patents, a thin, inner core of iodoester-radio-pacified polyurethane and a thicker outer core of plasticizer vinyl resin eliminates extraction problems with fluids passing through the core. In another feature, an inner core of nylon or polypropylene provides an outer jacket of iodoester radiopacified urethane or urethane-vinyl with stiffness, but much less tendency to kink in a multiwall construction; and such tubes are also easily manufactured in a co-tapered wall thickness construction in which the variations in twisting resistance provide enhanced ease of insertion through torturous body passages. A surface coating of silicone resin (Ser. No. 514,168) helps improve ease of insertion when properly formulated, while reducing thrombogenicity, but such constructions still can be improved, especially in terms of heat resistance.

More particularly, it is desirable to improve such structures in the following ways: to provide a more hydrophobic surface which allows fluid levels to be read correctly; to provide a surface with very little and, preferably, no filler exposed to minimize dangerous thrombogenic response; to provide a surface with reduced friction and wear; and to provide tubings and catheters made from such tubings which are more heat resistant and accordingly have improved sterilizability and service life.

It has now been found, and is the subject matter of the present invention, that if controlled amounts of platinum-cured silicone network polymers are employed in such compositions, tubings and catheters made therefrom will provide the above-enumerated advantages, and many others.

BRIEF DESCRIPTION OF THE DRAWINGS

The invention will be better understood by reference to the accompanying drawings in which.

DESCRIPTION OF THE INVENTION

In accordance with the present invention, there are provided catheters made from radiopaque compositions comprising:

(a) a resin which includes from 100 to 33 parts by weight of a thermoplastic polyurethane and from 0 to 67 parts of a polymer or copolymer of a halogenated vinyl monomer;

(b) a radiopacifier therefor consisting of a diiodobenzoate or a tetraiodobenzoate of the formula wherein $R^1$ is hydrogen or iodo, R is alkyl or alkoxyalkyl or a mixture of said compounds, said radiopacifier (b) comprising 10 to 40 parts by weight per 100 parts of (a) and (b); and, uniformly dispersed therein (c) a platinum-cured silicone network polymer, the amount of (c) comprising 8 to 30 parts by weight per 100 parts by weight of (a), (b) and (c).

Preferably, in component (b), each $R^1$ is iodo and R is (lower)alkyl or (lower)alkoxy (lower)alkyl. The most preferred radiopacifiers are n-butyl 2,3,4,6-tetraiodobenzoate, 2-ethoxyethyl 2,5-diiodobenzoate, or a mixture thereof.

Preferably, component (c) comprises the reaction product of

(i) an organic silicon compound having at least two silicon-bonded unsaturated groups per molecule, (ii) a silicon compound containing at least two silicon-bonded hydrogen atoms per molecule, and (iii) a small catalytically effective amount of a platinum-containing catalyst. Especially, preferably, the compositions will be essentially free of particulate materials, especially silica type fillers which are commonly employed with silicone polymers. The most preferred embodiments of component (c) will be those wherein (i) is of the formula:

(ii) is of the formula where R is selected from monovalent hydrocarbon radicals free of olefinic unsaturation, halogenated monovalent hydrocarbon radicals free of olefinic unsaturation and cyanoalkyl radicals; $R^1$ is selected from vinyl and allyl radicals; a has a value of from 1.0 to 2.5; b has a value of from 0.005 to 2.0; and the sum of a plus b is equal to from 1.005 to 3.0. In the most preferred embodiments, (iii) will be selected from chloroplatinic acid, platinum black, platinum adsorbed on a carrier, a platinum-olefin complex, a platinum-cyclopropane complex or a mixture of any of the foregoing.

In another aspect of the present invention there are provided catheters made from thermocurable radiopaque compositions comprising a Part A comprised of:

(a) a resin which includes from 100 to 33 parts by weight of a thermoplastic polyurethane and from 0 to 67 parts of a polymer of a halogenated vinyl monomer;

(b) a radiopacifier therefor consisting of a diiodobenzoate or a tetraiodobenzoate compound of the formula:

wherein $R^1$ is hydrogen or iodo, and R is alkyl or alkoxyalkyl or a mixture of said compounds, said radiopacifier comprising 10 to 40 parts by weight per 100 parts by weight of (a) and (b); and (c)(i) an organic silicon compound having at least two silicon-bonded unsaturated groups per molecule; and a Part B comprised of:

(a) a resin which includes from 100 to 33 parts by weight of a thermoplastic polyurethane and from 0 to 67 parts of a polymer of a halogenated vinyl monomer;

(b) a radiopacifier therefor consisting of a diiodobenzoate or a tetraiodobenzoate compound of the formula:

wherein $R^1$ is hydrogen or iodo, and R is alkyl or alkoxyalkyl or a mixture of said compounds, said radiopacifier comprising 10 to 40 parts by weight per 100 parts by weight of (a) and (b);

(c)(ii) a silicon compound containing at least two silicon-bonded hydrogen atoms per molecule; and (c)(iii) a small, catalytically effective amount of a platinum-containing catalyst, wherein the respective amounts of (c)(i), (ii) and (iii) are selected to provide from about 8 to about 30 parts by weight of a platinum-cured silicone network polymer, after having blended and thermo-formed parts A and B, per 100 parts by weight of the total composition. The preferred embodiments of the above thermocurable radiopaque compositions will be those wherein component (b) in part A and/or part B has as each $R^1$ an iodo and as R a (lower)alkyl or (lower)alkyl(lower)alkoxy. The most preferred embodiments will have (b), (c)(i)(ii)(iii) as previously described.

The thermoplastic polyurethanes are known to those skilled in this art. They are described in the Encyclopedia of Polymer Science and Technology, Vol. 11, pages 506–563, New York, Interscience Publishers, 1969, and especially on page 549. They are also commercially available from a number of suppliers, such as Hooker, as Rucothenes, especially 3713, and from Upjohn, as Pellethene, e.g., 75D, 85D and X-010155 80D, and from Mobay, as Texin.

Suitable vinyl resins are described in the above-mentioned U.S. Pat. No. 3,645,955. They are available from a number of sources, such as Escambia, Nos. 3225, 3250 and 3255; Diamond No. 450 and No. 500; Borden, 106PM and Dow Chemical Co. 100-4.

The radiopacifier compounds (b) can be made by procedures fully described in the above mentioned U.S. Pat. Nos. 3,645,955 and 3,361,700. In general, a 2,3,4,6-tetraiodobenzoyl halide or 2,5-diiodobenzoyl halide will be treated with an alkanol or alkoxyalkanol at ordinary temperatures, preferably in the presence of an acid acceptor. Alternatively, the free acid can be reacted with a sodium alkoxide or alkoxyalkoxide. The product can be recovered and purified in a known way, e.g., distillation.

The platinum-cured silicone network polymers employed herein are known in this art as components of interpenetrating polymer networks (IPN's). The compositions are blends of crosslinked polymers containing essentially no covalent bonds, or grafts, between them. In the present instance the IPN's are made by combining the thermoplastic polyurethane, alone, or in further combination with a vinyl resin, with crosslinkable silicon compounds. As will be shown hereinafter, by specific examples and by reference to patents, platinum-curable two-part silicone polymers are well known in this art. The formation of IPN-modified silicone polyurethane thermoplastics is discussed in Arkles, "IPN-Modified Silicone Thermoplastics" MD & DI, November, 1983, pages 66–70; Arkles and Carreno, "Silicone IPN Modified Thermoplastics", ANTEC 84 Conference Proceedings, New Orleans Apr. 30-May 3, 1984, pages 486–487; and Arkles, Ibid., pages 1080–1082.

Suitable silicon compounds containing at least two silicon-bonded hydrogen atoms per molecule which can be employed in the practice of the present invention have the formula:

$$(R)_a(H)_b SiO_{\frac{4-a-b}{2}}$$

where R is an organic radical attached to silicon through silicon-carbon linkages and free of aliphatic unsaturation. Among the organic radicals represented by R are monovalent hydrocarbon radicals free of olefinic unsaturation, halogenated monovalent hydrocarbon radicals free of olefinic unsaturation and cyanoalkyl radicals. More particularly, radicals represented by R include alkyl radicals, e.g., methyl, ethyl, propyl, butyl, octyl, etc. radicals; cycloalkyl radicals, e.g, cyclohexyl, cycloheptyl, etc. radicals; aryl radicals, e.g., phenyl, naphthyl, tolyl, xylyl, etc. radicals; aralkyl radicals, e.g, benzyl, phenylethyl, phenylpropyl, etc. radicals; halogenated radicals of the above types, including chloromethyl, chloropropyl, chlorophenyl, dibromophenyl, etc. radicals; and cyanoalkyl radicals, e.g., betacyanoethyl, gamma-cyanopropyl, beta-cyanopropyl, etc. radicals. Preferably, at least 50 percent of the R groups attached to silicon in the polysiloxane of the above formula are methyl radicals, with up to 50 percent of the R radicals being phenyl radicals.

The silicon compounds containing at least two silicon-bonded hydrogen atoms per molecule are well known in the art and include such materials as 1,3-dimethyldisiloxane, 1,1,3-trimethyldisiloxane, 1,1,3,3-tetramethyldisiloxane as well as higher polymers containing up to 100,000 or more silicon atoms per molecule. Also included within the scope of the above formula are cyclic materials such as the cyclic trimer or cyclic tetramer of methyl hydrogen siloxane. Such silicon compounds containing at least two silicon-bonded hydrogen atoms per molecule are described in Ashby, U.S. Pat. No. 3,159,601.

Suitable organic silicon compounds containing at least two silicon-bonded vinyl or allyl groups per molecule which can be employed in the practice of the present invention are also well known in the art and are characterized by the formula:

$$(R)_a(R^1)_b SiO_{\frac{4-a-b}{2}}$$

where R is as previously defined and $R^1$ is a member selected from vinyl and allyl radicals.

The preparation of these vinyl- or allyl-containing silicone compounds within the scope of the above formula is well known in the art. Included within the scope of the siloxanes of the above formula are low molecular weight materials such as 1,1-divinyltetramethyldisiloxane, 1,3-divinyltetramethyldisiloxane, 1,1,3-trivinyltrimethyldisiloxane, 1,1,3,3-tetravinyldimethyldisiloxane as well as higher polymers containing up to 100,000 or more silicon atoms per molecule. Also included within the scope of the unsaturated organopolysiloxanes within the scope of the above formula are cyclic materials containing silicon-bonded vinyl or allyl radicals, such as the trimer, tetramer or pentamer, of methylvinylsiloxane or methylallylsiloxane. Such organic silicon compounds containing at least two silicon bonded vinyl or allyl groups per molecule are described in Ashby, U.S. Pat. No. 3,159,601.

Any number of platinum-containing materials will catalyze the addition of silicon-bonded hydrogen atoms across the double bonds of compounds containing olefinic unsaturation. For example, Bailey, U.S. Pat. No. 2,970,150, shows the use of a platinum-on-charcoal catalyst, Speier, et al., U.S. Pat. No. 2,823,218, show the use of chloroplatinic acid, and Ashby, U.S. Pat. No. 3,159,622, shows the use of a platinum-cyclopropane complex. These and many other platinum-containing catalysts may be employed in the practice of the present invention. Preferred platinum-containing catalysts will be those described in Ashby, U.S. Pat. No. 3,159,601, which describes platinum-olefin complexes having the formulae:

$$[PtCl_2 \cdot Olefin]_2 \tag{1}$$

$$H[PtCl_3 \cdot Olefin] \tag{2}$$

wherein the olefin portion of (1) and (2) may be any olefin, but is preferably an alkene having from 2 to 8 carbon atoms, a cycloalkene having from 5 to 7 carbon atoms, or styrene.

When used in the appended claims, the term "alkyl" contemplates straight and branched chain radicals of from 1 to 30 carbon atoms, and the term "(lower)alkyl" contemplates such groups of from 1 to 6 carbon atoms.

The term "radioparent" plasticizer means a conventional plasticizer, for example, a dialkyl ester of aromatic or aliphatic polybasic acids, e.g., dioctyl adipate, which is commercially available from Rohm & Haas Co., as Monoplex DIOA. Also contemplated are epoxy plasticizers, such as Swift & Co.'s Epoxol 9-5. The term "heat stabilizer for said vinyl resin" embraces metallic salts, based on tin, calcium, zinc and the like. A suitable commercial heat stabilizer is based on calcium and zinc, available from Advance Division of Carlisle Chemical Works, as CZ-11C.

The formulations will be aided in some cases by the inclusion of lubricants such as metallic stearate, stearic acid, paraffin wax, mineral oil, etc., in conventional amounts. See U.S. Pat. No. 3,645,955, incorporated herein to minimize unnecessarily detailed description.

The compositions are prepared and converted into useful products by techniques well known to those skilled in the art.

In one manner of proceeding, the fluid ingredients, e.g., radiopaque compound(s) if liquid, are blended with the powdered solids, e.g., thermoplastic polyurethane resin, reactive curable silicone components, and, optionally, vinyl resin, stabilizers and platicizers, and then fused and mixed under pressure, e.g., in a Banbury-type mixer and discharged. Conventional 2-roll compounding techniques can also be used. The composition is cooled and granulated.

If extrusions are to be made, the granulated composition can be fed to a conventional machine, for example, a 30 millimeter Reifenhouser-type single screw extruder operated at suitable temperature, e.g., 280°–330° F. and the tubing or other shapes formed at a suitable rate, e.g., 7,000–10,000 feet per hour and cut automatically to length.

In another manner of proceeding, a thermocurable radiopaque composition comprising a part A and a part B, previously described, may be prepared and extruded, with or without precompounding either A and B, as mentioned above. Optionally, A and B will be precompounded and thereafter extruded under suitable conditions.

In still another manner of proceeding, multiwall tubing, of uniform or co-tapered wall construction, may be prepared by co-extruding a thermocurable radiopaque composition, comprising a part A and a part B, with another thermoplastic resin, or with another, differently formulated, thermocurable radiopaque composition comprising a part A and a part B.

Those skilled in the art will prepare a variety of thermocurable compositions comprising A and B wherein components (c)(i), (ii) and (iii), previously described, may be varied to effect different cure rates, degrees of cross-linking and/or physical/chemical properties of the finished compositions.

As is pointed out above, the compositions of this invention can be used for many various and diverse purposes, e.g, protective sheeting, surgeon's gloves, intubation sets, heart catheters, stomach tubes, nasal tubes, thoracic catheters and the like. The following examples primarily illustrate the use of these compositions in the form of single and multiple wall surgical tubing. However, from the foregoing description and the following examples and by reference to other well known teachings, the methods and modes by which the plasticized radiopaque urethane resin compositions of this invention can be formed into various other articles will be readily apparent to those skilled in the art.

The medical grade radiopaque tubing prepared as described in the following examples is non-toxic, non-reactive to tissue and may be sterilized by gas, cold sterilization solutions or heat sterilization techniques. The tubing is generally dispensed as such and the surgeon or trained technician will form it into catheters for roentgenography. For maximum convenience, the tubing can also be performed into articles and dispensed, e.g., as sterile disposable intravenous catheters.

By way of illustration, catheters according to this invention will be fabricated from the medical-surgical tubing of the following examples by operations comprising tip forming, tip finishing, shaping, side hole forming, and flaring. Before use they will be sterilized.

Those skilled in the art will prepare a variety of tip shapes. For internal mammary and axillary artery branches a three-quarter loop is formed in the distal end. For precutaneous arteriography and cerebral arteriography via femoral, a 45°–60° smooth bend will be formed in the distal end. Selective renal arteriography and celiac arteriography requires a one-half loop. Hepatic venography uses about a seven-eighths loop. For trans-sepal left-heart catheterization via the femoral vein, a three-quarter loop, like that above-described for mammary branches, but larger, is formed. On the other hand, abdominal aortography via brachial artery uses a rather large, one-third closed loop and thoracic aortography via the femoral artery uses the same shape but bigger. For lumbar aortography via the femoral artery the tip is straight out. For coronary arteriography, the end of the catheter is looped.

The heavier-walled tubing is formed into such typical shapes by inserting a forming wire within the tubing and heating in a tiny flame until visibly softened. By pulling from both ends the tubing is drawn to the wire and forms a uniform lumen around it. The tip is formed by cutting, e.g., with a razor blade, at the drawn diameter and is smoothly rounded in the flame. Next a precurved wire is inserted into the tube which is then immersed in hot water until the tubing softens. Quenching in cold water will cause the catheter to conform to the curve of the forming wire. Side hole or eye punching is accomplished by rotating a sharpened hole punch cannula under slight pressure. The holes should be large enough to expel contrast media without excess build up of injection pressures but should be no larger than ⅔ of the internal diameter of the tubing. The catheter is cut to the preselected length and flared. Heating in a small flame and rotating on a flaring tool produces a flare of the desired size. The catheter can be bonded at the flare, e.g., with epoxy cement, to a suitable hub. On the other hand, an adapter can be used to screw the catheter to a Luer-Lok stopcock, or the like.

DESCRIPTION OF THE PREFERRED EMBODIMENTS

The following non-limiting examples illustrate the present invention.

EXAMPLE 1

|  | 1 |
|---|---|
| PART A |  |
| Silicone-network polymer Composition (parts by weight) | (12%) |
| Resin, thermoplastic polyurethane, Pellethane 75 durometer | 1800 |
| 2-Ethoxyethyl-2,5-diiodobenzoate | 500 |
| Methylvinyl polysiloxane$^a$ | 315 |
| PART B |  |
| Silicone-network polymer Composition (parts by weight) | (12%) |
| Resin, thermoplastic polyurethane, Pellethane 75 durometer | 1800 |
| 2-Ethoxyethyl-2,5-diiodobenzoate | 500 |
| Methylhydrogen polysiloxane$^b$ | 315 |

-continued

|  | 1 |
|---|---|
| Platinum-olefin complex catalyst[c] | .031 |

[a] e.g., Methylvinylpolysiloxane fluid, 200 cps @25° C. comprising trimethylsilyl chain-stopping units and consisting of 2.0 mole percent methylvinylsiloxane units with the remainder of the diorganosiloxane units being dimethylsiloxane units. Example 8, U.S. Pat. No. 3,159,601.
[b] e.g., Methylhydrogenpolysiloxane fluid, 200 cps @25° C., comprising trimethylsilyl chain-stopping units and consisting of 2.0 mole percent methylhydrogensiloxane units with the remainder of the diorganosiloxane units being dimethylsiloxane units. Example 8, U.S. Pat. No. 3,159,601.
[c] (Pt Cl$_2$·C$_2$H$_4$)$_2$ Example 2, U.S. Pat. No. 3,159,601.

The compositions are mixed in a Banbury mixer for 4 minutes at 345° F. and for 2 minutes at 310° F., discharged, and granulated through a ⅛ in. screen.

Figure 2:
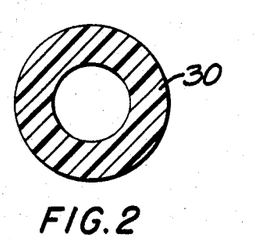
FIG. 2 is an enlarged cross-sectional view of radiopaque tubing according to this invention.

The granulated products of Parts A and B are dry blended at a 1:1 ratio and are thereafter extruded in a 30 mm. Reifenhauser screw extruder at 310°–330° F. into medical-surgical single wall tubing of the type shown in FIG. 2, 0.065 O.D.×0.044 I.D.−0.0105″, having properties eminently suitable for use as intubation sets and in catheter needles.

EXAMPLES 2–4

The general procedure of Example 1 is repeated, substituting the formulations enumerated in Table 1, and soft tubings according to this invention are obtained:

TABLE 1

| Radiopaque Soft Urethane/Silicone Compositions | | | |
|---|---|---|---|
| Example | 2 | 3 | 4 |
| Silicone-network polymer | (10%) | (25%) | (18%) |
| PART A | | | |
| Composition (parts by weight) | | | |
| Resin, thermoplastic polyurethane, Pellethane 75 D[a] | 1800 | 1200 | 1800 |
| X-010155 80D[b] | — | 600 | — |
| 2-Ethoxyethyl 2,5-diiodobenzoate | 900 | 1200 | 1038 |
| Methylvinyl polysiloxane[c] | 300 | 1000 | 632 |
| PART B | | | |
| Composition (parts by weight) | | | |
| Resin, thermoplastic polyurethane Pellethane 75 D[a] | 1800 | 1200 | 1800 |
| X-010155 80D[b] | — | 600 | — |
| 2-Ethoxyethyl 2,5-diiodobenzoate | 900 | 1200 | 1038 |
| Methylhydrogen polysiloxane[d] | 300 | 1000 | 632 |
| Platinum-olefin complex catalyst[e] | .030 | 0.100 | .063 |

[a] Upjohn Co.
[b] Upjohn Co.
[c-e] See Example 1, footnote a-c

EXAMPLES 5–7

The general procedure of Example 1 is repeated, substituting the formulations enumerated in Table 2, and medium hard tubings according to this invention are obtained:

TABLE 2

| Radiopaque Medium Hard Urethane/Silicone Compositions | | | |
|---|---|---|---|
| Example | 5 | 6 | 7 |
| Silicone-network polymer | (20%) | (15%) | (25%) |
| PART A | | | |
| Composition (parts by weight) | | | |
| Resin, thermoplastic polyurethane, Pellethane 75 D[a] | 900 | 982 | 600 |
| X-010155 80D[b] | 900 | 818 | 1200 |
| 2-Ethoxyethyl 2,5-diiodobenzoate | 1080 | 982 | 600 |
| n-Butyl 2,3,4,6-tetraiodobenzoate | — | — | 600 |
| Methylvinyl polysiloxane[c] | 720 | 492 | 1000 |
| PART B | | | |
| Composition (parts by weight) | | | |
| Resin, thermoplastic polyurethane Pellethane 75 D[a] | 900 | 982 | 600 |
| X-010155 80D[b] | 900 | 818 | 1200 |
| 2-Ethoxyethyl 2,5-diiodobenzoate | 1080 | 982 | 600 |
| n-Butyl 2,3,4,6-tetraiodobenzoate | — | — | 600 |
| Methylhydrogen polysiloxane[d] | 720 | 492 | 1000 |
| Platinum-olefin complex catalyst[e] | 0.072 | 0.049 | 0.100 |

[a] Upjohn Co.
[b] Upjohn Co.
[c-e] See Example 1, footnote a-c

EXAMPLES 8–10

The general procedure of Example 1 is repeated, substituting the formulations enumerated in Table 3, and hard tubings according to this invention are obtained.

TABLE 3

| Radiopaque Hard Urethane/Silicone Compositions | | | |
|---|---|---|---|
| Example | 8 | 9 | 10 |
| Silicone-network polymer | (25%) | (18%) | (10%) |
| PART A | | | |
| Composition (parts by weight) | | | |
| Resin, thermoplastic polyurethane, Pellethane 75 D[a] | — | 519 | 600 |
| X-010155 80D[b] | 1800 | 1281 | 1200 |
| 2-Ethoxyethyl 2,5-diiodobenzoate | 900 | 519 | 300 |
| n-Butyl 2,3,4,6-tetraiodobenzoate | — | 519 | 600 |
| Methylvinyl polysiloxane[c] | 900 | 624 | 300 |
| PART B | | | |
| Composition (parts by weight) | | | |
| Resin, thermoplastic polyurethane Pellethane 75 D[a] | — | 519 | 600 |
| X-010155 80D[b] | 1800 | 1281 | 1200 |
| 2-Ethoxyethyl 2,5-diiodobenzoate | 900 | 519 | 300 |
| n-Butyl 2,3,4,6-tetraiodobenzoate | — | 519 | 600 |
| Methylhydrogen polysiloxane[d] | 900 | 624 | 300 |
| Platinum-olefin complex catalyst[e] | 0.090 | 0.062 | 0.030 |

[a] Upjohn Co.
[b] Upjohn Co.
[c-e] See Example 1, footnote a-c

EXAMPLES 11–12

The general procedure of Example 1 is repeated, substituting the formulations enumerated in Table 4, and polyvinyl chloride/polyurethane tubings according to this invention are obtained.

TABLE 4

| Radiopaque Vinyl Chloride/Urethane/Silicone Compositions | | |
|---|---|---|
| Example | 11 | 12 |
| Silicone-network polymer | (10%) | (20%) |
| PART A | | |
| Composition (parts by weight) | | |
| Resin, thermoplastic polyurethane, Pellethane 75 D[a] | 964 | 783 |
| X-010155 80D[b] | — | 391 |
| Resin, thermoplastic polyvinyl-chloride, BK 80[c] | 836 | 626 |
| 2-Ethoxyethyl 2,5-diiodobenzoate | 482 | 1174 |
| n-Butyl 2,3,4,6-tetraiodobenzoate | 482 | — |
| Heat stabilizer, CZ-11C[d] | 16 | 16 |
| Plasticizer, Epoxol 905[e] | 112 | 141 |
| Methylvinyl polysiloxane[f] | 321 | 783 |

TABLE 4-continued

Radiopaque Vinyl Chloride/
Urethane/Silicone Compositions

| Example | 11 | 12 |
|---|---|---|
| PART B | | |
| Composition (parts by weight) | | |
| Resin, thermoplastic polyurethane, Pellethane 75 D[a] | 964 | 783 |
| X-010155 80D[b] | — | 391 |
| Resin, thermoplastic polyvinyl-chloride, BK 80[c] | 836 | 626 |
| 2-Ethoxyethyl 2,5-diiodobenzoate | 482 | 1174 |
| n-Butyl 2,3,4,6-tetraiodobenzoate | 482 | — |
| Heat stabilizer, CZ-11C[d] | 16 | 16 |
| Plasticizer, Epoxol 905[e] | 112 | 141 |
| Methylhydrogen polysiloxane[g] | 321 | 783 |
| Platinum-olefin complex catalyst[h] | 0.030 | 0.078 |

[a-b]Upjohn Co.
[c]Goodyear Co.
[d]Advance Division of Carlisle Chemical Works
[e]Swift & Co.
[f-h]See Example 1, footnote a-c.

EXAMPLE 13

Figure 1:
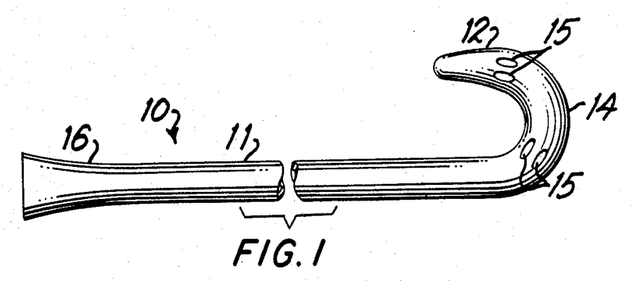
FIG. 1 is a longitudinal view of a catheter made from one form of the tubing made in accordance with the present invention and wherein, for illustrative purposes, the distal end is tapered and shaped to form a "J" tip, and the proximal end is flared.

The procedure of Example 1 is repeated, but the extruded tubing has an outer diameter of 0.098 inch and an inside diameter of 0.054 inch. This is formed into a finished catheter as illustrated in FIG. 1. Tubing 10 tapers down to a main body section 11 of substantially uniform cross-section to a curved J-shaped tip 12 at its distal end 14. One or more eyes or openings 15 are also provided in the distal end 14 for passages of fluids through the tubing 10. The proximal end of tubing 10 flares outwardly for receiving various equipment such as syringes for injecting fluids into the patient. The tapering and curvature of the tip, the flaring of the eyes and the flaring of the end are all effected by heated tools which utilize the thermoplastic properties of the extruded tubing. This single wall tubing has a cross-section as in FIG. 2 where reference numeral 30 illustrates the radiopaque composition of this invention.

Unlike catheters made from wholly vinyl resins, the catheter of this example readily resumes its shape after stretching and deforming.

EXAMPLE 14

A double wall radiopaque medical-surgical tubing is extruded in the temperature range of 310° F. to 330° F. in a conventional manner using conventional extrusion equipment having a biorifice tubular die for coextrusion of an inner core and an outer shell bonded to said inner tube. The tubing has an outer diameter of 0.098 inch and an inner diameter of 0.054 inch, and the inner tube has a thickness of 0.005 inch and the outer shell has a thickness of 0.017 inch. It will be understood that the dimensions given are illustrative but not limiting.

Figure 3:
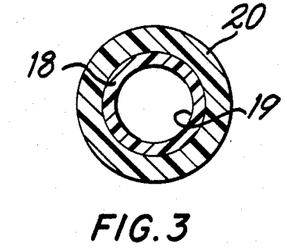
FIG. 3 is an enlarged cross-sectional view of tubing having a radiopaque inner core and a transparent outer shell.

Referring to FIG. 3, the thinner inner tube 18 comprises the two-part radiopaque thermoplastic polyurethane/silicone network composition of Example 1.

The thicker outer wall 20 comprises the following: 65 parts of poly(vinyl chloride) resin plasticized with 34 parts of epoxy plasticizer, Epoxol-9-5, stabilized with 1 part of calcium zinc stabilizer. This multiwall tubing is radiopaque of low cost construction, because of the PVC heavy wall, and is especially useful in larger sizes for stomach and nasogastric tubes. There is no possibility for PVC or plasticizer to elute into the fluid path (shown as 19 in FIG. 3).

Similar advantages are provided when a tubing is constructed according to these examples, but using nylon, and polypropylene, instead of vinyl in outer wall 20 of FIG. 3.

EXAMPLES 15-16

Figure 4:
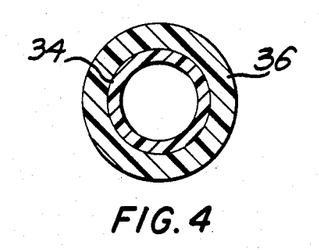
FIG. 4 is an enlarged cross-sectional view of tubing having a transparent core and a radiopaque outer shell.

Two multiwall tubes are made by the procedure of Example 14, except that the inner tube 34 (FIG. 4) comprises, nylon on the one hand, and polypropylene, on the other, and the outer shell 36 comprises the radiopaque two-part thermoplastic polyurethane/silicone network composition of Example 1. Each tubing provides catheters with superior torque characteristics in terms of resistance to kinking when passed through tortuous body passages.

EXAMPLES 17-18

Two co-tapered multiwall tubes are made by a modification of the procedure in Examples 15-16. The inner and outer layers are extruded concurrently and concentrically through annular concentric orifices of a multi-orifice extruder so as to bond the inner and outer layers together. The co-tapering of the inner and outer layers is obtained by varying the rate of extrusion of the inner and outer layers. See the above-mentioned Burlis et al. patent and Flynn, U.S. Pat. No. 4,250,072. The rate of extrusion of the inner layer gradually varies from a first rate to a second rate while the rate of extrusion of the outer layer gradually varies inversely for the inner layer.

Figure 6:
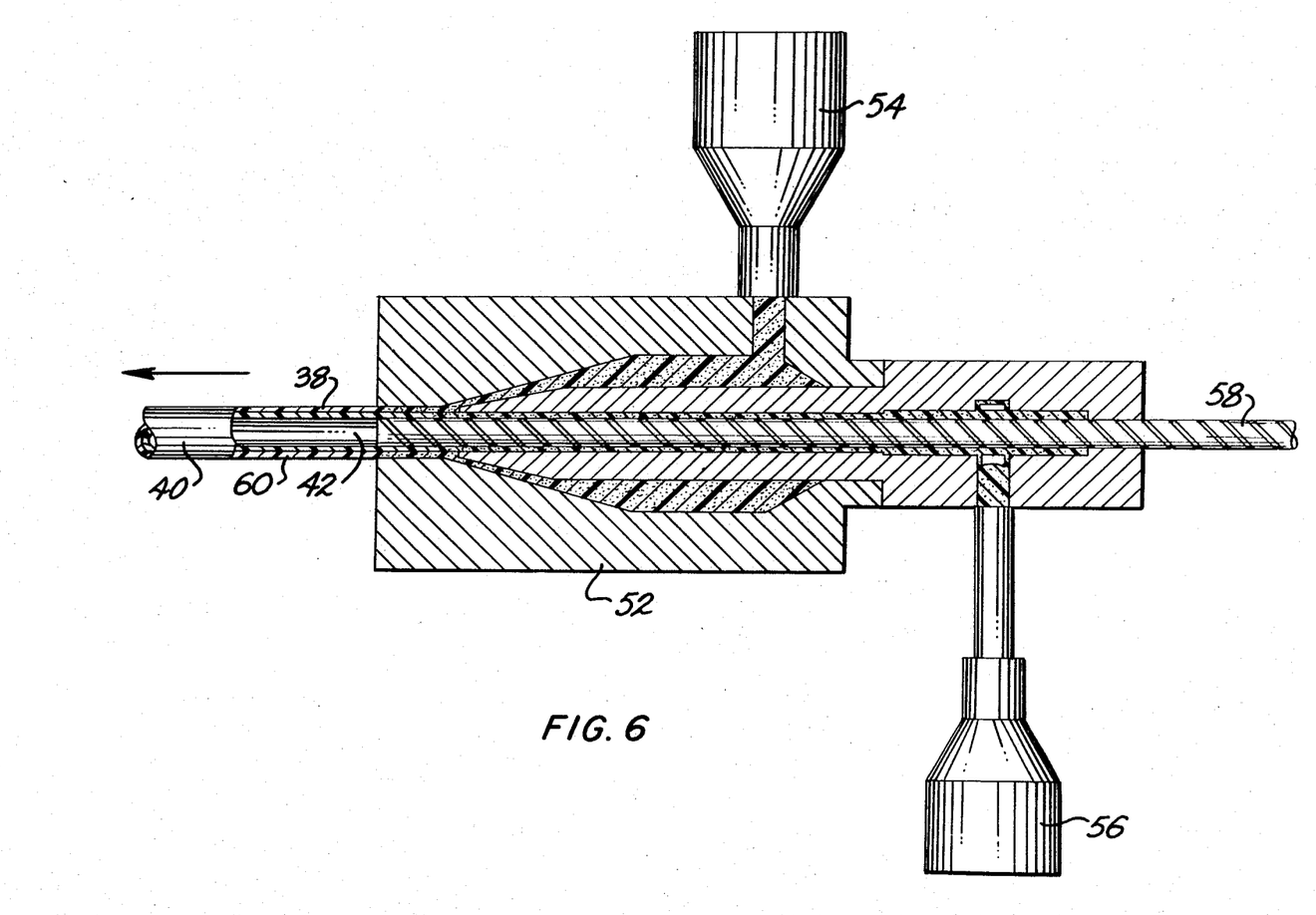

To exemplify further, reference is made to the accompanying drawing of FIG. 6. FIG. 6 is a schematic view of a bi-orifice extrusion head 52 from which tubing 40 is being extruded. Inner layer 60 is being discharged from the inner annular orifice of extrusion head 52. The thermoplastic composition for inner layer 60 is delivered to the extruder head 52 by extruder 56 at a decreasing, uniform rate. The outer layer 38 is being discharged from the concentric outer annular orifice of extruder head 52, the thermoplastic composition therefor being supplied by extruder 54 at an increasing rate inversely proportional to the declining rate of extruder 56. Since the tube 40 is being drawn by a Godet (not seen in FIG. 6) the inner layer 60 is tapering downward in thickness while the outer layer 38 is tapering upward in thickness. Air line 58 provides support for the thermoplastic walls 38, 60 and assists in defining lumen 42 during the extrusion. The increasing and decreasing rates of extrusion for inner and outer walls 60, 38 may be provided over any convenient length of time cycle to provide continuous lengths of co-tapered, multi-wall tubing of the invention. The rates of discharge from extruders 54 and 56 may then be reversed to begin the taper in the opposite direction, or the original first cycle may be repeated by synchronizing the speed of extrusion from the two extruders and then again increasing and decreasing the respective rates of discharge from each extruder 54, 56.

Figure 5:
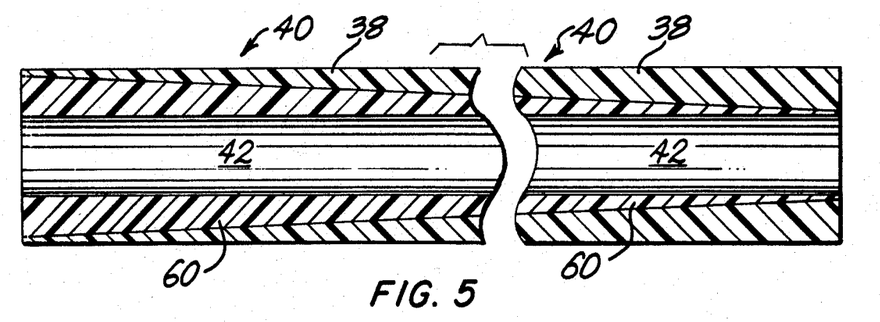
FIG. 5 is an enlarged, fragmentary cross-sectional view along the longitudinal axis of an embodiment tube of this invention having a transparent co-tapered core and a radiopaque, correspondingly co-tapered jacket, extruded as in FIG. 6.

The co-tapered tubings are illustrated in FIG. 5 in one embodiment.

In Example 17, inner wall 60 (FIG. 5) comprises nylon and outer wall 18 comprises the radiopaque two-part thermoplastic polyurethane/silicone network of Example 1.

In Example 18, inner wall 60 (FIG. 5) comprises polypropylene and outerwall 18 comprises the radiopaque two-part thermoplastic polyurethane/silicone network of Example 1.

Surgical catheters are formed from the respective tubings of Examples 17 and 18, and they exhibit a degree of flexibility and softening progressively changing from one end to the other. Such medical-surgical catheters have manipulative characteristics which are advantageously employed by the surgical operator in inserting, withdrawing and controlling the catheter.

EXAMPLE 19

A multiwall tube of co-taper construction is made following the preceeding example where the inner core is softer than the outer jacket. This is uniquely advantageous wherein higher torque is desired.

In Example 19, softer inner core 60 (FIG. 5) comprises a 55 to 65D durometer radiopaque two-part thermoplastic polyurethane/silicone network polymer containing 20 parts per 100 parts by weight of composition of 2-ethoxyethyl 2,5-diiodobenzoate; and harder outerwall 18 comprises a 75D durometer radiopaque two-part thermoplastic polyurethane/silicone network polymer and 20 parts per 100 parts by weight of composition of 2-ethoxyethyl 2,5-diiodobenzoate.

| Inner Core | |
|---|---|
| Silicone-network polymer (20%) | |
| Part A | |
| Composition (parts by weight) | |
| Resin, thermoplastic polyurethane (55-65 D durometer) | 1800 |
| Methylvinyl polysiloxane[a] | 200 |
| 2-Ethoxyethyl-2,5-diiodobenzoate | 500 |
| Part B | |
| Composition (parts by weight) | |
| Resin, thermoplastic polyurethane (55-65 D durometer) | 1800 |
| Methylhydrogen polysiloxane[b] | 200 |
| Platinum-olefin complex catalyst[c] | .02 |
| 2-Ethoxyethyl-2,5-diiodobenzoate | 500 |
| Outer Core | |
| Silicone-network polymer (20%) | |
| Part A | |
| Composition (parts by weight) | |
| Resin, thermoplastic polyurethane (75 D durometer) | 1800 |
| Methylvinyl polysiloxane[a] | 200 |
| 2-Ethoxyethyl-2,5-diiodobenzoate | 500 |
| Part B | |
| Composition (parts by weight) | |
| Resin, thermoplastic polyurethane (75 D durometer) | 1800 |
| Methylhydrogen polysiloxane[b] | 200 |
| Platinum-ethylene complex catalyst[c] | .02 |
| 2-Ethoxyethyl-2,5-diiodobenzoate | 500 |

[a-c]See Example 1, footnote a-c

EXAMPLE 20

A thin wall tubing (0.005" wall thickness) is extruded from the following compositions:

| Part A | |
|---|---|
| Silicone-network polymer (16.7%) | |
| Composition (parts by weight) | |
| Resin, thermoplastic polyurethane Rucothene 363 | 38.04 |
| Resin, poly(vinyl chloride) BK-80 Goodyear | 10.39 |
| n-Butyl 2,3,4,6-tetraiodobenzoate | 18.39 |
| 2-Ethoxyethyl 2,5-diiodobenzoate | 3.08 |
| Epoxy plasticizer, Epoxol 9-5 | 1.21 |
| Stabilizer CZ-11C | 0.17 |
| Bismuth oxychloride | 28.57 |
| Methylvinyl polysiloxane[a] | 20.00 |
| Part B | |

-continued

| Silicone-network polymer (16.7%) | |
|---|---|
| Composition (parts by weight) | |
| Resin, thermoplastic polyurethane Rucothene 363 | 38.04 |
| Resin, poly(vinyl chloride) BK-80 Goodyear | 10.39 |
| n-Butyl 2,3,4,6-tetraiodobenzoate | 18.39 |
| 2-Ethoxyethyl 2,5-diiodobenzoate | 3.08 |
| Epoxy plasticizer, Epoxol 9-5 | 1.21 |
| Stabilizer CZ-11C | 0.17 |
| Bismuth oxychloride | 28.57 |
| Methylhydrogen polysiloxane[b] | 20.00 |
| Platinum-olefin complex catalyst[c] | 0.006 |

[a-c]See Example 1, footnote a-c.

In comparison with tubing without bismuth oxychloride, this tubing has an enhanced tensile strength and higher radiopacity. The procedure is repeated substituting equal parts by weight of barium sulfate per 100 parts by weight of the composition for the bismuth oxychloride. Again higher tensile strength and higher radiopacity are obtained.

Such tubes are especially useful to provide miniballoon catheters.

Obviously, the compositions of this invention provide tubings with many advantages. With respect to polytetrafluoroethylene catheters, the present invention overcomes an inability to provide a range of soft to hard catheters in a variety of wall thicknesses. This leads to a reduction in mechanical trauma induced by stiffer catheters. Also polytetrafluoroethylene is limited in its ability to accept adequate loading of radiopaque media to be clearly visible, if a small section is lost or fragmented,. Furthermore, both the urethanes and the urethane-vinyls can be co-extruded according to this invention with a hard vinyl or urethane liner, which on draw down produces a thin hard knife edge impervious to peel back or fragmentation seen with the polytetrafluoroethylene catheters.

With respect to prior art vinyl tubings, drug vehicle compatibility with the present tubings is extended in numbers and concentration, and iodine extraction reduced, because of the ability of the urethanes and PVC-urethanes to lock in the iodo-esters. For example, they exhibit no spew or exudation when tested for four days at 100% humidity.

The foregoing patents and publications are incorporated herein by reference. Obviously, many variations will suggest themselves to those skilled in this art in light of the above, detailed description. All such obvious variations are within the full intended scope of the appended claims.

What is claimed is:

1. A medical-surgical catheter formed from tubing comprising:
   (a) a resin which includes from 100 to 33 parts by weight of a thermoplastic polyurethane and from 0 to 67 parts of a polymer of a halogenated vinyl monomer;
   (b) a radiopacifier therefor consisting of a diiodobenzoate or a tetraiodobenzoate compound of the formula:

wherein $R^1$ is hydrogen or iodo, and R is alkyl or alkoxyalkyl or a mixture of said compounds, said radiopacifier (b) comprising 10 to 40 parts by weight per 100 parts by weight of (a) and (b); and, uniformly dispersed therein (c) a platinum-cured silicone network polymer, the amount of (c) comprising 8 to 30 parts by weight per 100 parts by weight of (a), (b) and (c), wherein said medical-surgical catheter provides a surface that is essentially free of exposed filler.

2. A medical-surgical catheter as defined in claim 1 wherein, in said radiopacifier (b), each $R^1$ is iodo and R is (lower)alkyl or (lower)alkoxy(lower)alkyl.

3. A medical-surgical catheter as defined in claim 1 wherein said radiopacifier (b) is n-butyl 2,3,4,6-tetraiodobenzoate.

4. A medical-surgical catheter as defined in claim 1 wherein said radiopacifier (b) is 2-ethoxyethyl 2,5-diiodobenzoate.

5. A medical-surgical catheter as defined in claim 1 wherein said radiopacifier (b) is a mixture of n-butyl 2,3,4,6-tetraiodobenzoate and 2-ethoxyethyl 2,5-diiodobenzoate.

6. A medical-surgical catheter as defined in claim 1 which is essentially free of particulate silica.

7. A medical-surgical catheter as defined in claim 1 wherein said platinum-cured silicone network polymer (c) comprises the reaction product of
(i) an organic silicon compound having at least two silicon-bonded unsaturated groups per molecule,
(ii) a silicon compound containing at least two silicon-bonded hydrogen atoms per molecule, and
(iii) a small, catalytically effective amount of a platinum-containing catalyst.

8. A medical-surgical catheter as defined in claim 7 wherein component (i) is of the formula:

and component (ii) is of the formula:

where R is selected from monovalent hydrocarbon radicals free of olefinic unsaturation, halogenated monovalent hydrocarbon radicals free of olefinic unsaturation, cyanoalkyl radicals or a mixture of any of the foregoing; $R^1$ is selected from vinyl radicals, allyl radicals or a mixture thereof; a has a value of from 1.0 to 2.5; b has a value of from 0.005 to 2.0; and the sum of a plus b is equal to from 1.005 to 3.0.

9. A medical-surgical catheter as defined in claim 8 wherein component (iii) is selected from chloroplatinic acid, platinum black, platinum adsorbed on a carrier, a platinum-olefin complex, a platinum-cyclopropane complex or a mixture of any of the foregoing.

10. A medical-surgical catheter comprising:
(1) an interior tubular portion of a radiopaque composition comprising:
(a) a resin which includes from 100 to 33 parts by weight of a thermoplastic polyurethane and from 0 to 67 parts of a polymer of a halogenated vinyl monomer;
(b) a radiopacifier therefor consisting of a diiodobenzoate or a tetraiodobenzoate compound of the formula:

wherein $R^1$ is hydrogen or iodo, and R is alkyl or alkoxyalkyl or a mixture of said compounds, said radiopacifier (b) comprising 10 to 40 parts by weight per 100 parts by weight of (a) and (b); and uniformly dispersed therein (c) a platinum-cured silicone network polymer, the amount of (c) comprising 8 to 30 parts by weight per 100 parts by weight of (a), (b) and (c); and (2) a concentric outer shell comprising:
(a) a polymer of a halogenated vinyl monomer which further includes a minor proportion of a radiopaque plasticizer for said vinyl polymer,
(b) nylon, or
(c) polypropylene, wherein said medical-surgical catheter provides a surface that is essentially free of exposed filler.

11. A medical-surgical catheter as defined in claim 10 wherein, in said interior tubular portion, said resin component (a) comprises a thermoplastic polyurethane and said radiopacifier comprises 2-ethoxyethyl 2,5-diiodobenzoate.

12. A medical-surgical catheter as defined in claim 10 wherein interior tubular portion (1) is relatively thin and outer shell portion (2) is relatively thick.

13. A medical-surgical catheter comprising (1) an interior tubular portion, of a relatively softer, as measured by durometer hardness, composition, as defined in claim 10 and (2) a concentric outer shell, of a relatively harder, as measured by durometer hardness composition, as defined in claim 10.

14. A medical-surgical catheter as defined in claim 10 wherein, in said radiopacifier (b), each $R^1$ is iodo and R is (lower) alkyl or (lower)alkoxy(lower)alkyl.

15. A medical-surgical catheter as defined in claim 10 wherein said radiopacifier (b) is n-butyl 2,3,4,6-tetraiodobenzoate.

16. A medical-surgical catheter as defined in claim 10 wherein said radiopacifier (b) is 2-ethoxyethyl 2,5-diiodobenzoate.

17. A medical-surgical catheter as defined in claim 10 wherein said radiopacifier (b) is a mixture of n-butyl 2,3,4,6-tetraiodobenzoate and 2-ethoxyethyl 2,5-diiodobenzoate.

18. A medical-surgical catheter as defined in claim 10 which is essentially free of particulate silica.

19. A medical-surgical catheter as defined in claim 10 wherein the concentric outer shell (2) of the vinyl resin (a), nylon (b) or polypropylene (c) further includes (d) a platinum-cured silicone network polymer, the amount of (d) comprising 4 to 24 parts by weight per 100 parts by weight of (a) plus (d), (b) plus (d) or (c) plus (d).

20. A medical-surgical catheter as defined in claim 19 wherein component (c) of the interior tubular portion and component (d) of the concentric outer shell (2) comprise the reaction product of
 (i) an organic silicon compound having at least two silicon-bonded unsaturated groups per molecule,
 (ii) a silicon compound containing at least two silicon-bonded hydrogen atoms per molecule, and
 (iii) a small, catalytically effective amount of a platinum-containing catalyst.

21. A medical-surgical catheter as defined in claim 20 wherein component (i) is of the formula:

and component (ii) is of the formula:

where R is selected from monovalent hydrocarbon radicals free of olefinic unsaturation, halogenated monovalent hydrocarbon radicals free of olefinic unsaturation, cyanoalkyl radicals or a mixture of any of the foregoing; $R^1$ is selected from vinyl radicals, allyl radicals or a mixture thereof; a has a value of from 1.0 to 2.5; b has a value of from 0.005 to 2.0; and the sum of a plus b is equal to from 1.005 to 3.0.

22. A medical-surgical catheter as defined in claim 21 wherein component (iii) is selected from chloroplatinic acid, platinum black, platinum adsorbed on a carrier, a platinum-olefin complex, a platinum-cyclopropane complex or a mixture of any of the foregoing.

23. A medical-surgical catheter comprising:
 (1) an interior tubular portion comprising:
  (a) nylon or
  (b) polypropylene, each containing
  (c) 4 to 24 parts by weight, based upon the weight of the nylon or polypropylene, of a platinum-cured silicone network polymer, and
 (2) a concentric outer shell of a radiopaque composition comprising:
  (a) a resin which includes from 100 to 33 parts by weight of a thermoplastic polyurethane and from 0 to 67 parts of a polymer of a halogenated vinyl monomer;
  (b) a radiopacifier therefor consisting of a diiodobenzoate or a tetraiodobenzoate compound of the formula:

wherein $R^1$ is hydrogen or iodo, and R is alkyl or alkoxyalkyl or a mixture of said compounds, said radiopacifier (b) comprising 10 to 40 parts by weight per 100 parts by weight of (a) and (b); and, uniformly dispersed therein,
  (c) a platinum-cured silicone network polymer, the amount of (c) comprising 5 to 25 parts by weight per 100 parts by weight of (a), (b) and (c), wherein said medical-surgical catheter provides a surface that is essentially free of exposed filler.

24. A medical-surgical catheter as defined in claim 23 wherein said interior tubular portion (1) comprises nylon containing 4 to 24 parts by weight, based upon the weight of the nylon, of a platinum-cured silicone network polymer.

25. A medical-surgical catheter as defined in claim 23 wherein said interior tubular portion (1) comprises polypropylene containing 4 to 24 parts by weight, based upon the weight of the polypropylene, of a platinum-cured silicone network polymer.

26. A medical-surgical catheter as defined in claim 23 wherein, in said radiopacifier (b), each $R^1$ is iodo and R is (lower)alkyl or (lower)alkoxy(lower)alkyl.

27. A medical-surgical catheter as defined in claim 23 wherein said radiopacifier (b) is n-butyl 2,3,4,6-tetraiodobenzoate.

28. A medical-surgical catheter as defined in claim 23 wherein said radiopacifier (b) is 2-ethoxyethyl 2,5-diiodobenzoate.

29. A medical-surgical catheter as defined in claim 23 wherein said radiopacifier (b) is a mixture of n-butyl 2,3,4,6-tetraiodobenzoate and 2-ethoxyethyl 2,5-diiodobenzoate.

30. A medical-surgical catheter as defined in claim 23 which is essentially free of particulate silica.

31. A medical-surgical catheter as defined in claim 23 wherein said platinum-cured silicone network polymer (c) of the interior tubular portion (1) and of the concentric outer shell (2) comprise the reaction product of
 (i) an organic silicon compound having at least two silicon-bonded unsaturated groups per molecule,
 (ii) a silicon compound containing at least two silicon-bonded hydrogen atoms per molecule, and
 (iii) a small, catalytically effective amount of a platinum-containing catalyst.

32. A medical-surgical catheter as defined in claim 31 wherein component (i) is of the formula:

and component (ii) is of the formula:

where R is selected from monovalent hydrocarbon radicals free of olefinic unsaturation, halogenated monovalent hydrocarbon radicals free of olefinic unsaturation, cyanoalkyl radicals or a mixture of any of the foregoing; $R^1$ is selected from vinyl radicals, allyl radicals or a mixture thereof; a has a value of from 1.0 to 2.5; b has a value of from 0.005 to 2.0; and the sum of a plus b is equal to from 1.005 to 3.0.

33. A medical-surgical catheter as defined in claim 32 wherein component (iii) is selected from chloroplatinic acid, platinum black, platinum adsorbed on a carrier, a platinum-olefin complex, a platinum-cyclopropane complex or a mixture of any of the foregoing.

34. A medical-surgical catheter as defined in claim 23 having a first point along its length and a second point along its length spaced apart from said first point, the thickness of said interior tubing portion (1) tapering as it passes from said first point to said second point and the thickness of said outer shell (2) tapering inversely to the taper of said interior tubing as it passes from said first point to said second point.

* * * * *